(12) United States Patent
Shawl

(10) Patent No.: US 11,623,799 B2
(45) Date of Patent: Apr. 11, 2023

(54) CONTAMINATION FREE LIQUID-SPRAY DISPENSING APPARATUS AND METHOD OF USE

(71) Applicant: Theodros Shawl, Oakland, CA (US)

(72) Inventor: Theodros Shawl, Oakland, CA (US)

( * ) Notice: Subject to any disclaimer, the term of this patent is extended or adjusted under 35 U.S.C. 154(b) by 313 days.

(21) Appl. No.: 17/159,144

(22) Filed: Jan. 27, 2021

(65) Prior Publication Data
US 2022/0234793 A1 Jul. 28, 2022

(51) Int. Cl.
| | | |
|---|---|---|
| B65D 47/20 | (2006.01) | |
| B65D 25/48 | (2006.01) | |
| B65D 47/12 | (2006.01) | |
| B05B 1/02 | (2006.01) | |
| B05B 1/14 | (2006.01) | |
| G01F 11/26 | (2006.01) | |
| B05B 11/04 | (2006.01) | |
| B65D 83/00 | (2006.01) | |

(52) U.S. Cl.
CPC ............ *B65D 47/2031* (2013.01); *B05B 1/02* (2013.01); *B05B 1/14* (2013.01); *B05B 11/04* (2013.01); *B65D 25/48* (2013.01); *B65D 47/12* (2013.01); *B65D 83/0094* (2013.01); *G01F 11/263* (2013.01)

(58) Field of Classification Search
CPC .... B65D 47/2031; B65D 25/48; B65D 47/12; B65D 83/0094; B05B 1/02; B05B 1/14; B05B 11/04; G01F 11/263
USPC ................. 239/337, 340, 350, 377; 222/207
See application file for complete search history.

(56) References Cited

U.S. PATENT DOCUMENTS

| | | | |
|---|---|---|---|
| 4,088,248 A * | 5/1978 | Blake | F04B 43/02 222/207 |
| 6,419,168 B1 * | 7/2002 | Thieleke | B25C 1/08 239/350 |
| 8,845,895 B1 | 9/2014 | Ghiassi | |
| 2002/0020756 A1 * | 2/2002 | Yahav | B65D 83/262 239/350 |
| 2006/0163187 A1 | 7/2006 | Kopinetz | |

* cited by examiner

*Primary Examiner* — Steven J Ganey

(57) ABSTRACT

The present invention is a fluid dispensing apparatus, and method of use, e.g. for mouthwash and medicine, for dispensing a sterile liquid in single doses to prevent bacterial growth from un-used portions pored back into the apparatus. The apparatus has a hollow flexible cap enclosure surrounding a one-way valve inside of a bladder and a push rubber surface for liquid release. When the cap is removed, both the container body and the cap remain sealed from exposure to contaminates. Liquid is first dispensed from the container by inverting the container until a quantity of sterile liquid collects in the cap. The container is then positioned in an upright position and the fluid filled cap is removed from the container. The cap is then inverted again and a pushbutton pressed to dispense sterile liquid from a cap spray nozzle without requiring the user's lips to touch the cap.

20 Claims, 8 Drawing Sheets

CONTAMINATION FREE LIQUID-SPRAY DISPENSING APPARATUS AND METHOD OF USE

FIELD OF THE INVENTION

The present invention relates generally to liquid containers. More particularly, the invention relates to a mouthwash containing vessel designed to eliminate contaminating backflow and dispense a predetermined quantity of liquid.

BACKGROUND OF THE INVENTION

Mouthwash and other anti-bacterial and sanitizing agents in liquid form continue to use plastic bottles to contain the liquids. This leads people to store partially consumed plastic bottles for repeated later use. This behavior can lead to bacterial and other types of contamination and growth in the unused liquid. Consuming the remaining liquid in the bottles can present health risks related to ingesting liquid with bacteria growth from backwash. In response to this issue, there are items that reduce the backflow of liquid into the bottle through the use of one-way valves, such as U.S. Patent Application Publication No. 20060/0163187A1 entitled "Drinking Container with One-way Valve", and using filtration systems, such as U.S. Pat. No. 8,845,895 entitled "Reusable water bottle with disposable cap and filter". However, these devices may still expose the contents of the bottle to bacteria transported through the physical contact with the individual's lips.

A frequent problem with mouthwash containers is that the user initially pours out more liquid than needed, e.g. into the bottle cap. The desired amount is then used and the remainder is poured back into the bottle. The bottle cap is removed to ingest the mouthwash, this usually requiring the user to place his lips on the cap inner surface. Even if the mouthwash is antibacterial, contaminants and debris eventually gather in and around the container and on the cap resulting in an unsanitary condition, especially if the mouthwash container is shared by two or more people.

Similarly, antiseptic and liquid medicinal bottles, such as in cases of children's syrups, nutritional supplements and oral medications, have a tendency to be used repeatedly over a period of time without proper disinfecting measures, thus allowing pathogens to harvest around the tip of the bottle and inside the cap exponentially over time. Oral, vaginal, upper respiratory tract and even some gastro-intestinal tract microorganisms including *E. coli, Candida albicans, Staphylococcus aureus* and certain strains of influenza to name a few. Researchers have shown bacteria growth in 90% of reusable water bottles enter a bottle every time the cap is removed.

What is needed within the consumable liquids bottle industry is a plastic bottle that is sealed to block the entry of pathogens and other contaminates into the bottle's main container and its cap, even when the cap is removed and/or used then reattached to the container. The bottle should still be able to easily dispense a measured dose into the cap, and the user then pour or spray the sterile liquid into their mouth. The cap and the main container also need to maintain sterility on the inside surface by not being exposed to the air, or requiring the user to touch the inner surface with their fingers or lips, even when the cap is removed.

SUMMARY OF THE INVENTION

The present invention comprises various embodiments of a contamination free bottle apparatus comprising a main body container and cap for dispensing a sterile liquid in single doses as a spray. The cap comprises a hollow flexible enclosure surrounding a one-way valve. Liquid is first dispensed from the container by inverting the apparatus until a quantity of liquid flows from the container main body to collect in the cap enclosure. The apparatus is then positioned in an upright position and the fluid filled cap enclosure is removed from the container. The cap enclosure is then inverted and squeezed to dispense sterile liquid as a spray. Both the cap enclosure and the container comprise a flat engagement surface to seal their inner compartment from contamination by external pathogens and debris when the two are separated.

In one or more embodiments, the present invention comprises a contamination free liquid dispensing apparatus, and method of use, comprising: a) a main container body having: i) a top and a bottom, the top of said main body having a flat engagement surface from which a hollow upstanding post with a fluid outlet extends, the post in fluid communication with a first circular aperture formed therein; b) a dispensing cap enclosure having: i) a top and a bottom, the bottom of said dispensing enclosure having a flat engagement surface with a second circular aperture, said dispensing cap enclosure removably attached to said main container body and wherein the first and second apertures are aligned to allow a sterile liquid to pass from the main container body into the dispensing cap enclosure; ii) a spray nozzle positioned on a bottom corner of the dispensing cap enclosure. The sterile fluid is able to be expressed from said dispensing cap enclosure as a spray by inverting said main container body to allow liquid to accumulate in the dispensing cap enclosure, then removing the dispensing cap enclosure and inverting it without spillage to spray the fluid from the spray nozzle; and the sterile fluid within said apparatus is not contaminated by exposure to air, or a user's mouth or fingers, or a backflow from the dispensing cap enclosure into the main container body.

In one or more embodiments, the present invention comprises an apparatus and a method of dispensing a quantity of a sterile fluid from a dispensing apparatus without contaminating the sterile fluid or the inner walls of the dispensing apparatus, comprising: 1) providing a liquid dispensing apparatus comprising: a) a main container body having a top and a bottom, the top of said main container body having a flat engagement surface from which an upstanding post extends, the post in fluid communication with an opening formed therein; b) a dispensing cap enclosure removably attached to said main container body and having a first opening for receiving said upstanding post, said enclosure having a hollow main body for receiving a quantity of sterile liquid, said liquid contained inside a bladder, which lines said hollow main body; c) a second opening in said dispensing cap enclosure covered by an actuator for expressing sterile fluid from said cap enclosure; and d) whereby the sterile fluid is expressed from said cap closure as a spray by inverting said main container body to allow the sterile liquid to accumulate in the cap enclosure, then removing the cap enclosure and depressing the actuator.

In an embodiment, the apparatus further comprises atop the upstanding post on the main container body is positioned a dispensing outlet with an endpoint opening, the upstanding post acting as a conduit to allow fluid to flow from the main body through to fill the dispensing enclosure.

In an embodiment, the endpoint opening is covered by a one-way valve able to prevent fluid from dripping back out of the dispensing outlet when the dispensing cap enclosure is removed from the main container body; and able to prevent the sterile fluid from re-entering the main container body when the dispensing cap enclosure is re-attached.

In an embodiment, the dispensing cap enclosure further comprises a bladder lining the cap inner walls and attached to the one-way valve, the bladder able to provide a seal to keep the liquid from leaking when the apparatus is inverted, and to provide a pressure to eject a spray from the spray nozzle.

In an embodiment, the apparatus further comprises an opening in the dispensing cap enclosure flat engagement surface that is covered by an actuator for expressing under pressure the fluid from said dispensing cap enclosure.

In an embodiment, the spray nozzle in the dispensing cap enclosure further comprises a plurality of small apertures able to produce an aerosolized mist when the liquid is expressed from the dispensing cap enclosure.

In an embodiment, the apparatus further comprises on the dispensing cap enclosure one or more graduated markings able to allow a user to measure a fluid dose when said apparatus is turned upside down for filling of the fluid.

In an embodiment, the dispensing enclosure is made of flexible transparent material allowing a user to see the amount of the fluid within, and to apply pressure to said cap enclosure to facility ejecting the spray.

In an embodiment, one or both sidewalls of the main container body are curved inward to enable a user to grasp said apparatus.

An object of the present invention is to provide an improved liquid dispensing apparatus that can dispense a predetermined quantity of liquid, and wherein the liquid is sterile.

Another object is to provide an improved liquid dispensing apparatus that can eliminate backflow into the liquid container from the cap.

Another object is to provide an improved liquid dispensing apparatus that has a cap enclosure that can remain in sealed relation to a main body container until all of the stored liquid is dispensed, so that each dose is free of pathogen and debris contamination.

Another object is to provide an improved liquid dispensing apparatus that dispenses sterile liquid in a spray form.

BRIEF DESCRIPTION OF THE DRAWINGS

The above and other features, aspects, and advantages of the present disclosure will become better understood with regard to the following description, appended claims, and accompanying drawing herein.

FIG. 5A illustrates turning the apparatus upside down to fill the cap.

FIG. 5B illustrates removing the cap, where both the cap bottom and the container top side are sealed from contaminates and to prevent dripping and spilling of the sterile fluid due to the two parallel flat engagement surfaces.

FIG. 5C illustrates turning the cap upside down again without any spillage.

FIG. 5D illustrates a user being able to pour and/or squeeze the cap sterile fluid contents from the spray nozzle into their mouth without touching to their lips.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited.

As used herein, the term "sterile" refers to the liquid inside the apparatus of the present invention being free of pathogens and debris, including liquid and airborne contaminates, because both the main body container and the cap enclosure are sealed from exposure to the air and user contamination, even when separated; and because the backflow of liquid, such as for a partially used dose, is prevented from pouring back into the container from the cap.

The present invention is directed to various embodiments of a liquid dispensing apparatus that stores and dispenses as a spray a sterile liquid, such as mouthwash or medicine, as depicted in the exemplary embodiment(s) of FIGS. 1-5D.

Figure 1:
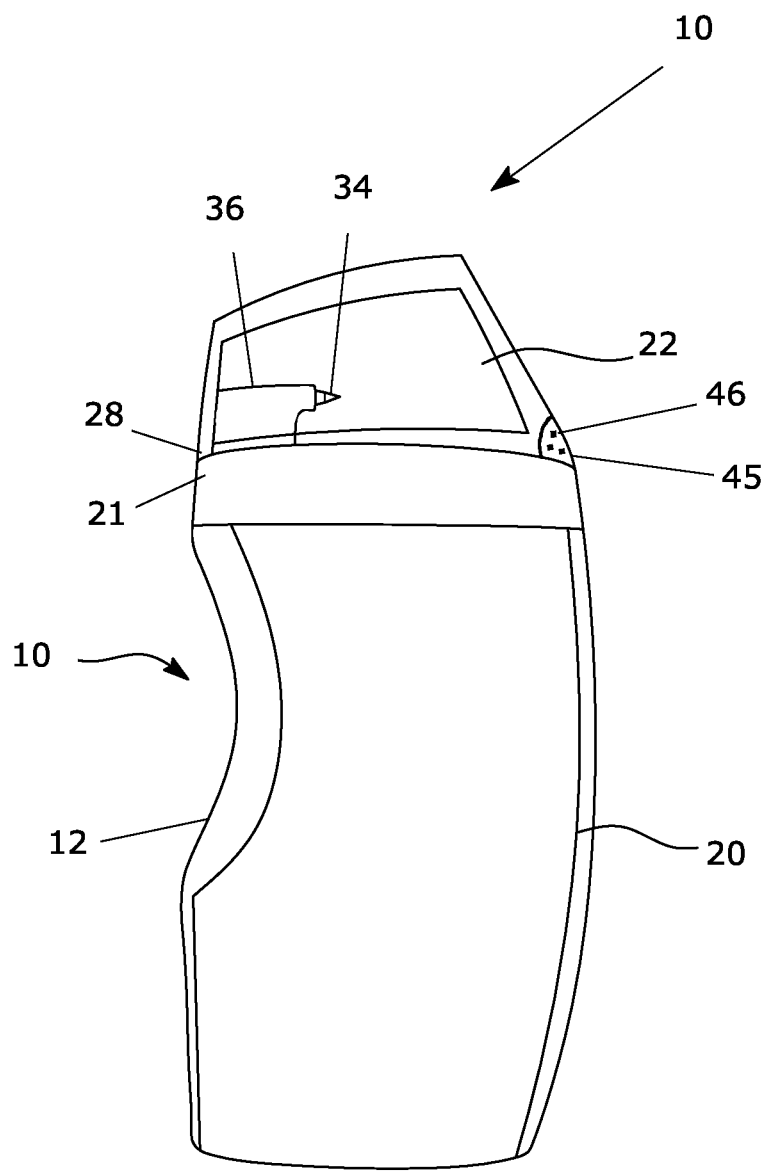
FIG. 1 illustrates a side view of an exemplary liquid dispensing apparatus.
Figure 5A:
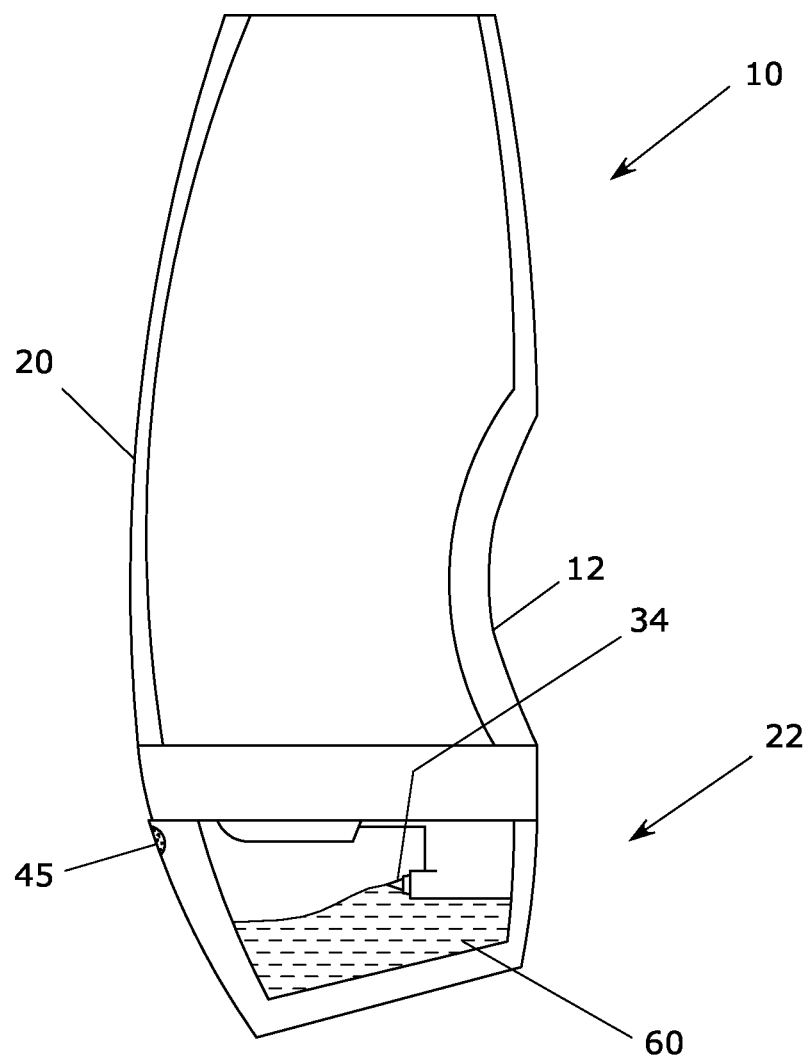
FIGS. 5A-5D illustrate the method of use steps for the contamination free liquid spray apparatus.
Figure 5B:
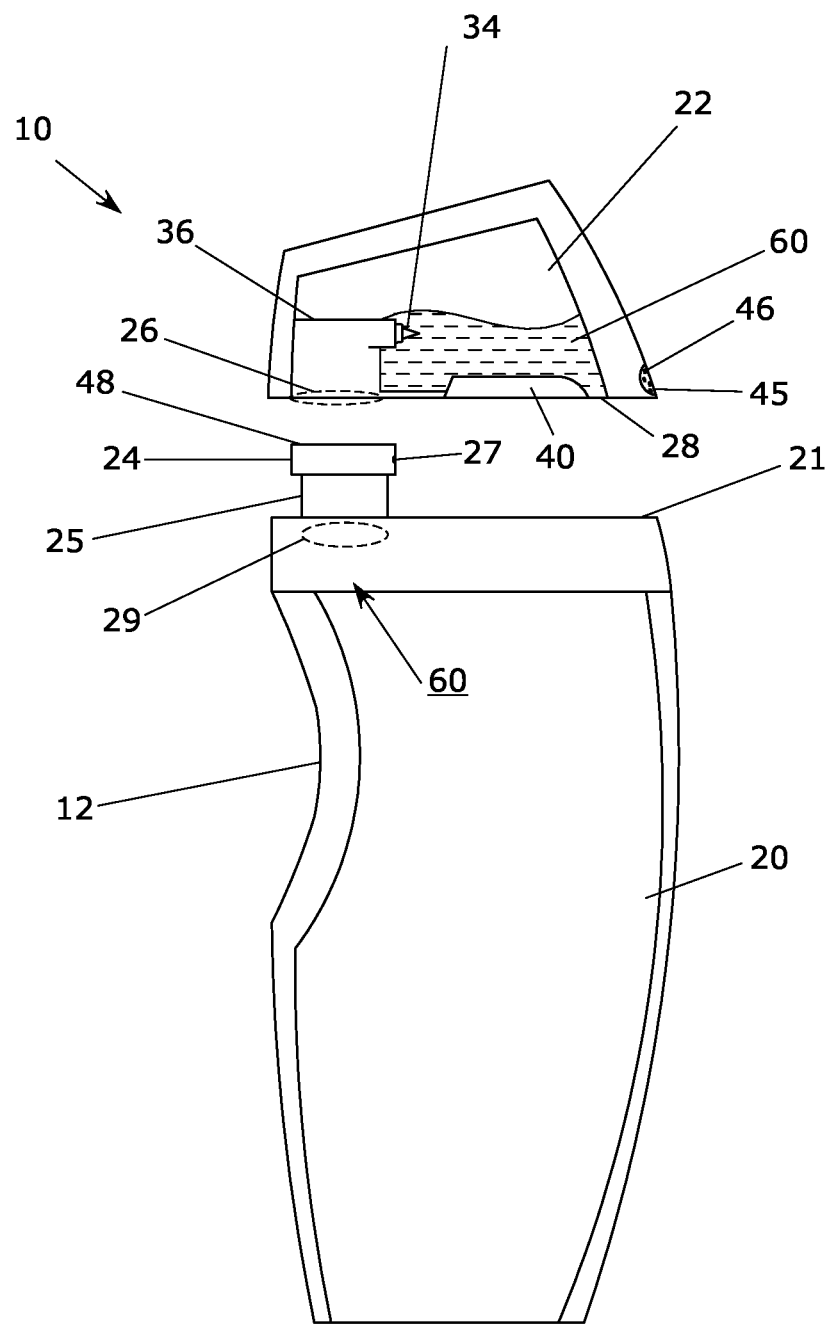

As illustrated in FIGS. 1, 5A, and 5B, the liquid dispenser apparatus is generally indicated by the numeral 10, and it comprises: 1) a container having an elongated main body 20 for containing a volume of fluid; and 2) a separable cap enclosure 22. In the exemplary embodiment, one side of the container body 20 is curved inward, so as to fit a user's fingers to assist in holding the vessel. Other shapes are envisioned within the scope of the present invention, such as both container sides are curved or straight.

In accordance with one aspect of the invention, the dispenser 10 is used to dispense a predetermined amount of liquid into a sealed cap enclosure 22, e.g. when turned upside down by allowing gravity to pull fluid down from container 20 into the cap 22. The apparatus may be used to dispense any sterile fluid that needs to be used or consumed in controlled or dosed amounts without contaminating the dispensed fluid or the fluid remaining in the container, and has particular utility for dispensing mouthwash and oral rinses without contact with the user's mouth.

Figure 2:
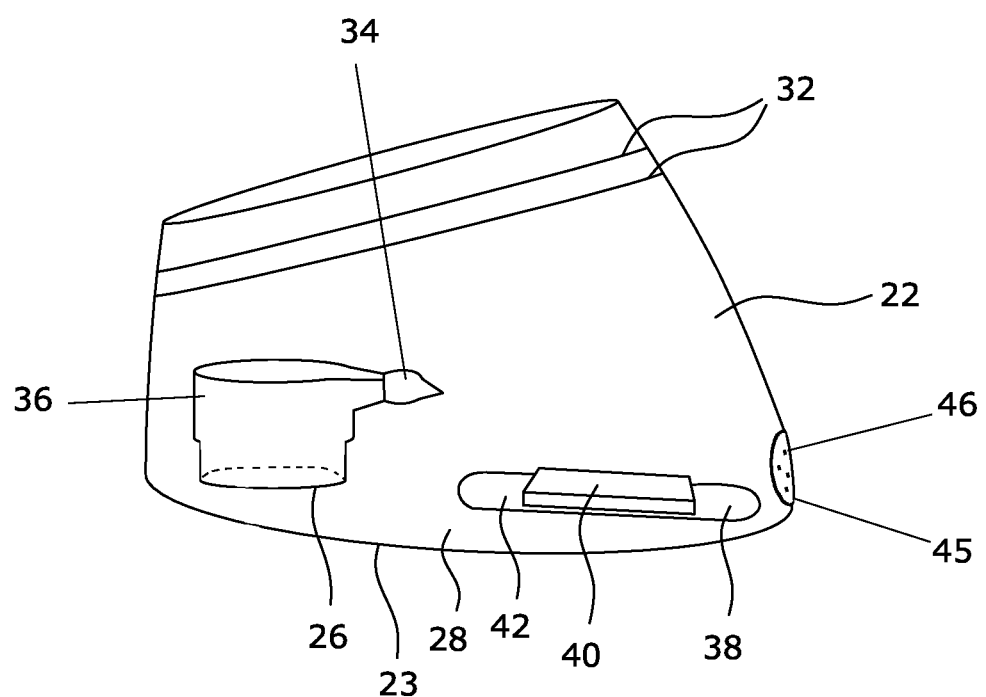
FIG. 2 illustrates a perspective view of the cap detailing the dispensing mechanism.
Figure 3:
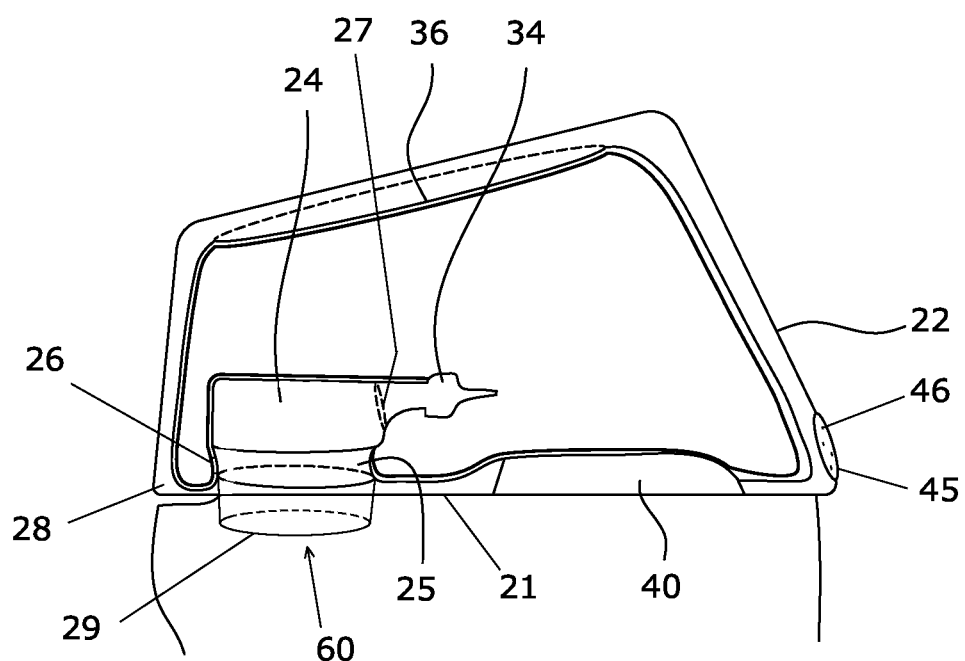
FIG. 3 illustrates a longitudinal cross-sectional view of the cap detailing the dispensing mechanism, one-way valve, and bladder.
Figure 4:
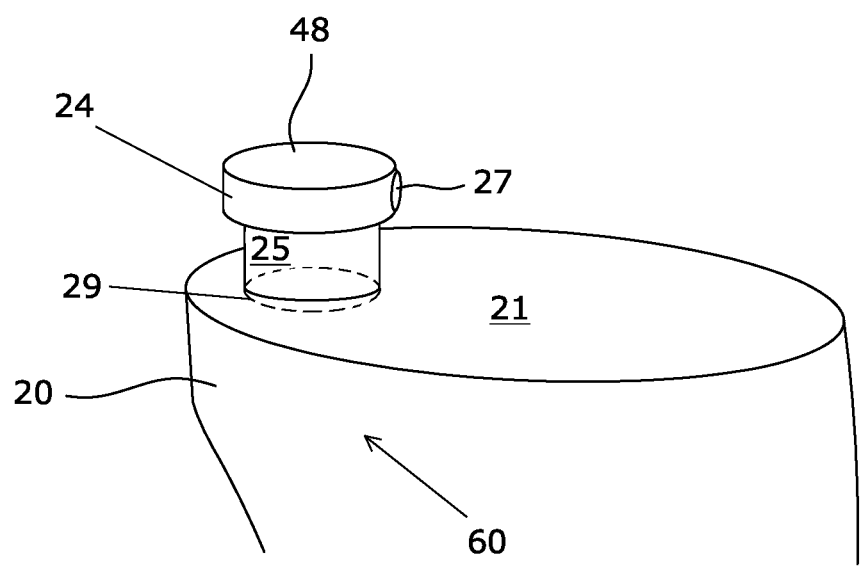
FIG. 4 illustrates a top perspective view of the top of the container with the cap removed showing the sealed top surface with a dispensing outlet, and how the flat engagement surface seals the container from contaminates.

Referring now to FIGS. 2-4, the sealing and dispensing mechanism within the cap and container are shown in detail. The main body of container 20 terminates at its upper end in a flat engagement surface 21 upon which the dispensing enclosure 22 (i.e. the cap) rests. Both the main body 20 and the enclosure 22 have a flat engagement surface, 21 and 28, respectively, that touch and/or are positioned in parallel when the cap is on the container. Then when the cap enclosure 22 is removed, the inside of the main body 20 and the cap enclosure 22 remain sealed from being contaminated, and prevent fluid from dripping or spilling from the cap. The edge 23 of the cap enclosure is also sized for snap fit engagement with the edge of the container's flat engagement surface 21, as is known in the art.

As illustrated in FIG. 4, an upstanding dispensing outlet 24 is formed on the container engagement surface 21. In one embodiment, the main body 20, the flat engagement surface 21, and the dispensing outlet 24 are formed via injection molding, as a single unitary piece. The upstanding dispensing outlet 24 is positioned to slide into a similarly shaped outlet within a cap bladder 36, which lines the cap's inner walls to prevent fluid seepage.

As further illustrated in FIG. 3, a substantially circular aperture 26 is formed in the cap flat engagement surface 28 of the enclosure 22, and is aligned with a second circular opening 29 formed in the top surface of the main container body 20. The apertures 26, 29 are of matching sizes and aligned to allow the container's dispensing outlet 24 and post 25 to be inserted therethrough aperture 26 into bladder 36. The fluid is thus able to pass from the main body container 20 through aperture 29, then aperture 26, through post 25 and into the outlet 24. As shown in FIG. 4, dispensing outlet 24 positioned atop the upstanding post 25, terminates with an increased diameter portion 48 having an endpoint opening 27, the post acting as a conduit to allow fluid to flow through to the opening 27 and into a one-way valve 34, which is connected to the bladder 36 (see FIG. 3).

As previously stated, the apparatus 10 is designed to allow the user to dispense or squeeze out a desired amount of liquid in a spray or flowing liquid form. To that end, cap enclosure 22 is transparent and may include graduated markings 32 to allow the user to measure the dose when the apparatus is turned upside down for filling. Alternatively, the user may just fill the entire cap enclosure 22 and pour or spray out the contents (e.g. into a user's mouth without touching their lips or skin) until the cap enclosure is empty, and then refill it. Cap enclosure 22 is filled by inverting the main body 20 and allowing the contents of the container 20 to flow into the cap enclosure 22 by way of one-way valve 34. The valve 34 is formed at the end of bladder 36, the bladder lining the enclosure 22 to provide a way to seal to keep the liquid from leaking when the vessel is inverted, and also to provide pressure to create a spray and express the liquid from the enclosure 22. The bladder 36 and valve 34 may be created as an integrated single component, and installed by insertion through the (third) substantially oval shaped aperture or opening 38 formed for pushbutton 40 (see FIG. 2).

Pushbutton 40 is located on the cap flat engagement surface 28, next to aperture 26. It is flat and flexible enough to be deflected and cause pressure to build within cap enclosure 22, in cooperation with the bladder 36. The pushbutton 40 is made from rubber or similar flexible material, which can deform or deflect substantially without permanently deforming. As illustrated in FIG. 2, pushbutton 40 is situated approximately centrally of a larger portion of relatively thin flexible material 42, which material is the same as that used for the pushbutton 40. Thus pushbutton 40 is essentially an actuator for expressing fluid from the enclosure. Depressing pushbutton 40 also causes deflection of the material 42 to generate pressure (by way of displacement) for expelling the contents of the enclosure 22. Full depression of the pushbutton 40 will always displace the same amount of liquid and thus the amount of spray or dosage can be metered using this method, e.g., 2 pushes for ⅛ ounce of fluid.

Figure 5C:
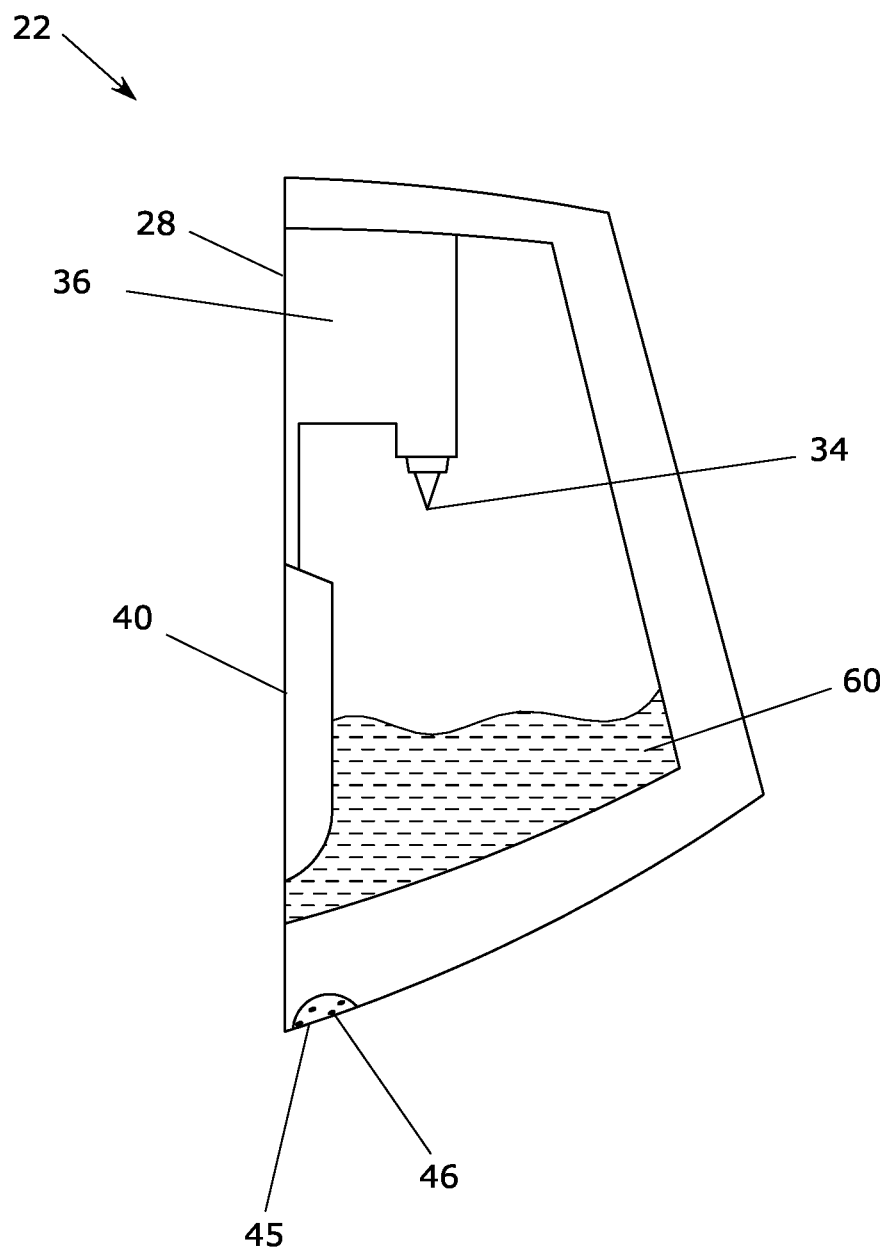
Figure 5D:
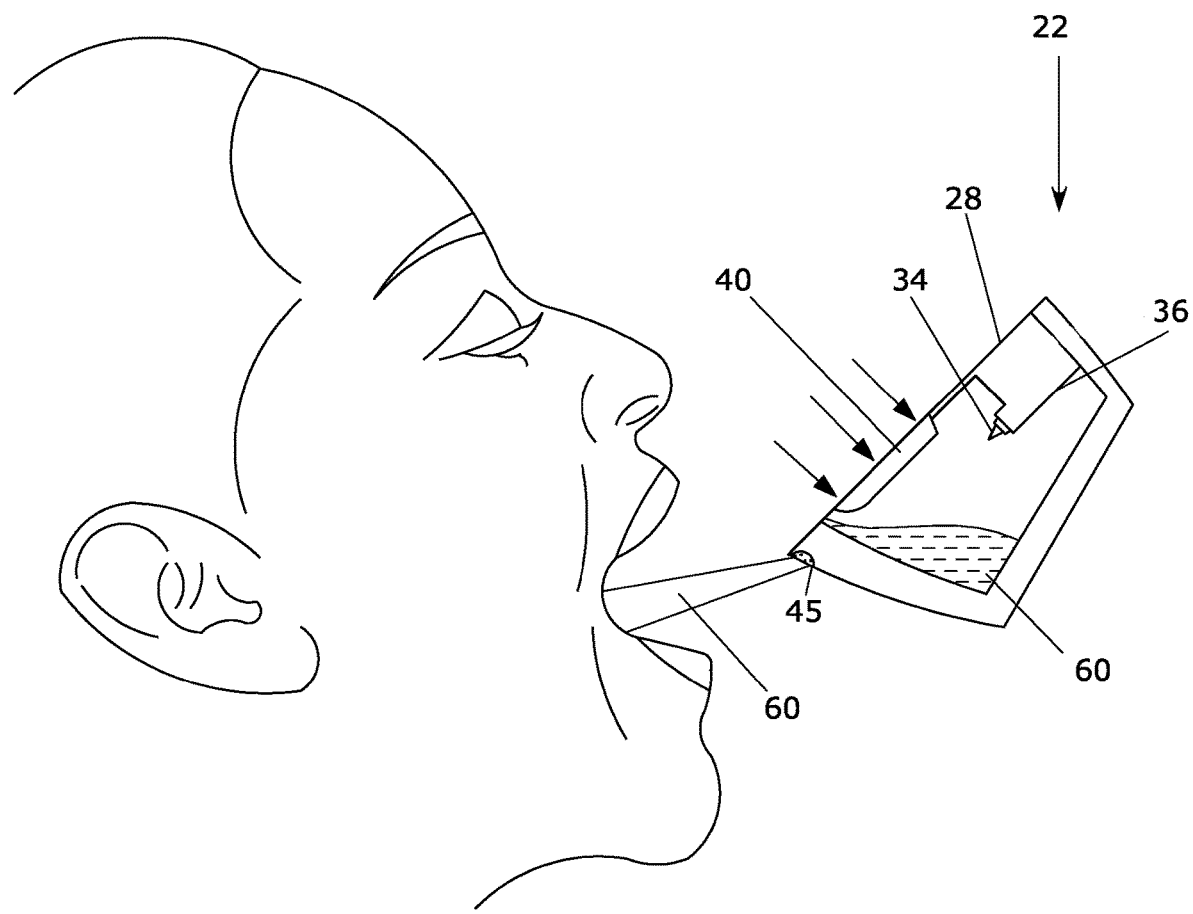

Spray or dispensing nozzle 45 is formed in the sidewall and/or bottom corner of the cap enclosure 22, the dispensing nozzle having an array of fine apertures 46 to produce an aerosolized mist when liquid is expressed from the enclosure 22 (see FIGS. 2, 3, 5D).

A key aspect of the invention is that the contents of the apparatus can be completely consumed without backflow or other debris (from opening the vessel) contaminating the liquid contents. While spray bottles can ordinarily perform this function, they are particularly cumbersome when dispensing mouthwash or oral rinses. Accordingly, even if mouthwash or breath freshener is dispensed from a spray bottle, the bottle is always made relatively small. Otherwise, mouthwash, oral rinses, breath fresheners etc., are usually dispensed from a bottle cap. The present invention allows the user to fill and then detach a relatively small cap enclosure 22, and then dispense a measured amount of liquid in the desired orifice.

Method of Use

As illustrated in FIGS. 5A-5D, the method of use basically comprises: inverting container 20; filling the cap enclosure 22 with the sterile fluid; removing the cap enclosure 22 from the container 20, wherein the cap is sealed so no spillage is possible; pouring or spraying the fluid contents from the cap into a user's mouth or onto skin without touching the user; and reattaching the empty or partially filled cap to the container while preventing any remaining fluid from leaving the cap and draining back into the container.

In FIG. 5A, the user inverts the container 20 allowing a desired amount of fluid to fill cap enclosure 22. The user may squeeze the sides of the container to accelerate the fluid filling. Graduated markings 32 on the cap 22 may be used to gauge the amount of fluid, or the user may opt to fill the entire enclosure 22.

In FIG. 5B, the enclosure 22 is then removed from the main body container for dispensing, and itis flipped upside down (see rotation in FIG. 5C showing no spillage due to the flat engagement surface 28).

In FIG. 5D, the user then simply depresses pushbutton 40 to dispense or spray the contents of the enclosure 22 out of spray nozzle 45, which is located on the bottom corner of the cap 22, opposite aperture 26.

CONCLUSION

It will be appreciated that the methods and apparatuses of the present disclosure can be incorporated in the form of a variety of embodiments, only a few of which are disclosed herein. It will also be apparent for the expert skilled in the field that other embodiments exist and do not depart from the spirit of the invention. Thus, the described embodiments are illustrative and should not be construed as restrictive.

Accordingly, the preceding exemplifications merely illustrate the principles of the various embodiments. It will be appreciated that those skilled in the art will be able to devise various arrangements which, although not explicitly described or shown herein, embody the principles of the embodiments and are included within its spirit and scope. Furthermore, all examples and conditional language recited herein are principally intended to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the various embodiments, therefore, is not intended to be limited to the exemplary embodiments shown and described herein.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described.

The term "about" as used herein refers to a value within 10% of the underlying parameter (i.e., plus or minus 5%), and use of the term "about" at the beginning of a string of values modifies each of the values (i.e., "about 1, 2 and 3" refers to about 1, about 2 and about 3).

Thus, it should be understood that although the present technology has been specifically disclosed by representative embodiments and optional features, modification and variation of the concepts herein disclosed may be resorted to by those skilled in the art, and such modifications and variations are considered within the scope of this technology.

As used herein, the term "substantially" refers to approximately the same shape as stated, and recognizable by one of ordinary skill in the art.

Trademarks: the product names used in this document are for identification purposes only; and are the property of their respective owners.

What is claimed is:

1. A contamination free liquid dispensing apparatus (10) comprising:
   a) a main container body (20) having:
      i) a top and a bottom, the top of said main body having a flat engagement surface (21) from which a hollow upstanding post (25) with a liquid outlet extends, the post in liquid communication with a first circular aperture (29) formed therein;
   b) a dispensing cap enclosure (22) having:
      i) a top and a bottom, the bottom of said dispensing cap enclosure having a flat engagement surface (28) with a second circular aperture (26), said dispensing cap enclosure removably attached to said main container body and wherein the first and second apertures are aligned to allow a sterile liquid to pass from the main container body into the dispensing cap enclosure;
      ii) a spray nozzle (45) positioned on a bottom corner of the dispensing cap enclosure;
   c) whereby the sterile liquid is able to be expressed from said dispensing cap enclosure as a spray by inverting said main container body to allow the sterile liquid to accumulate in the dispensing cap enclosure, then removing the dispensing cap enclosure and inverting it without spillage to spray the sterile liquid from the spray nozzle; and
   d) wherein the sterile liquid within said apparatus is not contaminated by exposure to air, or a user's mouth or fingers, or a backflow from the dispensing cap enclosure into the main container body.

2. The contamination free liquid dispensing apparatus of claim 1, wherein atop the upstanding post (25) on the main container body is positioned a dispensing outlet (24) with an endpoint opening (27), the upstanding post acting as a conduit to allow the sterile liquid to flow from the main body through to fill the dispensing cap enclosure.

3. The contamination free liquid dispensing apparatus of claim 2, wherein the endpoint opening (27) is covered by a one-way valve (34) able to prevent the sterile liquid from dripping back out of the dispensing outlet (24) when the dispensing cap enclosure (22) is removed from the main container body (20); and able to prevent the sterile liquid from re-entering the main container body (20) when the dispensing cap enclosure (22) is re-attached.

4. The contamination free liquid dispensing apparatus of claim 3, wherein the dispensing cap enclosure (22) further comprises a bladder (36) lining the cap inner walls and attached to the one-way valve (34), the bladder able to provide a seal to keep the liquid from leaking when the apparatus is inverted, and to provide a pressure to eject a spray from the spray nozzle.

5. The contamination free liquid dispensing apparatus of claim 1, further comprising an opening (38) in said dispensing cap enclosure flat engagement surface (28), said opening covered by an actuator (40) for expressing under pressure the sterile liquid from said dispensing cap enclosure (22).

6. The contamination free liquid dispensing apparatus of claim 1, wherein the spray nozzle (45) in the dispensing cap enclosure (22) further comprises a plurality of small apertures (46) able to produce an aerosolized mist when the liquid is expressed from the dispensing cap enclosure (22).

7. The contamination free liquid dispensing apparatus of claim 1, further comprising on the dispensing cap enclosure (22) one or more graduated markings (32) able to allow a user to measure a liquid dose when said apparatus is turned upside down for filling of the sterile liquid.

8. The contamination free liquid dispensing apparatus of claim 1, wherein the dispensing cap enclosure is made of flexible transparent material allowing a user to see the amount of the fluid within, and to apply pressure to said dispensing cap enclosure (22) to facility ejecting the spray.

9. The contamination free liquid dispensing apparatus of claim 1, wherein one or both sidewalls of the main container body are curved inward to enable a user to grasp said apparatus.

10. A contamination free liquid dispensing apparatus (10) comprising:
   a) a main container body (20) having a top and a bottom, the top of said main container body having a flat engagement surface (21) from which an upstanding post (24) extends, the post in liquid communication with an opening (29) formed therein;
   b) a dispensing cap enclosure (22) removably attached to said main container body (20) and having a first opening (26) for receiving said upstanding post, said dispensing cap enclosure having a hollow main body for receiving a quantity of sterile liquid, said sterile liquid contained inside a bladder (36) which lines said hollow main body;
   c) a second opening (38) in said dispensing cap enclosure covered by an actuator (40) for expressing the sterile liquid from said dispensing cap enclosure; and
   d) whereby the sterile liquid is expressed from said dispensing cap enclosure as a spray by inverting said main container body to allow the sterile liquid to accumulate in the dispensing cap enclosure, then removing the dispensing cap enclosure and depressing the actuator.

11. A method of dispensing a sterile fluid from a dispensing apparatus without contaminating the sterile fluid or the inner walls of the dispensing apparatus, comprising:
   1) providing a fluid dispensing apparatus comprising:
      a) a main container body (20) having:
         i) a top and a bottom, the top of said main body having a flat engagement surface (21) from which a hollow upstanding post (25) with a fluid outlet extends, the post in fluid communication with a first circular aperture (29) formed therein;

b) a dispensing cap enclosure (22) having:

i) a top and a bottom, the bottom of said dispensing cap enclosure having a flat engagement surface (28) with a second circular aperture (26), said dispensing cap enclosure removably attached to said main container body and wherein the first and second apertures are aligned to allow a sterile fluid to pass from the main container body into the dispensing cap enclosure;

ii) a spray nozzle (45) positioned on a bottom corner of the dispensing cap enclosure;

c) whereby the sterile fluid is able to be expressed from said dispensing cap enclosure as a spray by inverting said main container body to allow the sterile fluid to accumulate in the dispensing cap enclosure, then removing the dispensing cap enclosure and inverting it without spillage to spray the sterile fluid from the spray nozzle; and d) wherein the sterile fluid within said apparatus is not contaminated by exposure to air, or a user's mouth or fingers, or a backflow from the dispensing cap enclosure into the main container body;

2) inverting said apparatus, and allowing a quantity of the sterile fluid to flow into the dispensing cap enclosure;
3) removing the dispensing cap enclosure from the main container body without exposing an inner apparatus walls or the sterile fluid to contaminates;
4) inverting the dispensing cap enclosure and positioning the spray nozzle near a site of administration;

5) ejecting from the dispensing cap enclosure, the sterile fluid as a spray into or onto a site of administration without touching said site; and 6) replacing the dispensing cap enclosure onto the main container body.

12. The method of claim 11, wherein atop the upstanding post (25) on the main container body is positioned a dispensing outlet (24) with an endpoint opening (27), the upstanding post acting as a conduit to allow the sterile fluid to flow from the main body through to fill the dispensing cap enclosure.

13. The method of claim 12, wherein the endpoint opening (27) is covered by a one-way valve (34) able to prevent the sterile fluid from dripping back out of the dispensing outlet (24) when the dispensing cap enclosure (22) is removed from the main container body (20); and able to prevent the sterile fluid from re-entering the main container body (20) when the dispensing cap enclosure (22) is re-attached.

14. The method of claim 13, wherein the dispensing cap enclosure (22) further comprises a bladder (36) lining the cap inner walls and attached to the one-way valve (34), the bladder able to provide a seal to keep the sterile fluid from leaking when the apparatus is inverted, and to provide a pressure to eject a spray from the spray nozzle.

15. The method of claim 11, further comprising an opening (38) in said dispensing cap enclosure flat engagement surface (28), said opening covered by an actuator (40) for expressing under pressure the sterile fluid from said dispensing cap enclosure (22).

16. The method of claim 11, wherein the spray nozzle (45) in the dispensing cap enclosure (22) further comprises a plurality of small apertures (46) able to produce an aerosolized mist when the sterile fluid is expressed from the dispensing cap enclosure (22).

17. The method of claim 11, further comprising on the dispensing cap enclosure (22) one or more graduated markings (32) able to allow a user to measure a fluid dose when said apparatus is turned upside down for filling of the sterile fluid.

18. The method of claim 11, wherein the dispensing cap enclosure is made of flexible transparent material allowing a user to see the amount of the sterile fluid within, and to apply pressure to said dispensing cap enclosure (22) to facility ejecting the spray.

19. The method of claim 11, wherein one or both sidewalls of the main container body are curved inward to enable a user to grasp said apparatus.

20. A method of dispensing a quantity of a sterile fluid from a dispensing apparatus without contaminating the sterile fluid or the inner walls of the dispensing apparatus, comprising:

1) providing a fluid dispensing apparatus comprising:

a) a main container body (20) having a top and a bottom, the top of said main container body having a flat engagement surface (21) from which an upstanding post (24) extends, the post in fluid communication with an opening (29) formed therein;

b) a dispensing cap enclosure (22) removably attached to said main container body (20) and having a first opening (26) for receiving said upstanding post, said dispensing cap enclosure having a hollow main body for receiving a quantity of sterile fluid, the sterile fluid contained inside a bladder (36) which lines said hollow main body;

c) a second opening (38) in said dispensing cap enclosure covered by an actuator (40) for expressing the sterile fluid from said dispensing cap enclosure; and d) whereby the sterile fluid is expressed from said dispensing cap closure as a spray by inverting said main container body to allow the sterile fluid to accumulate in the cap enclosure, then removing the dispensing cap enclosure and depressing the actuator;

2) inverting the apparatus, and allowing the sterile fluid to flow into the dispensing cap enclosure;

3) removing the dispensing cap enclosure from the main container body without exposing an inner apparatus walls or the sterile fluid to contaminates;

4) inverting the dispensing cap enclosure and positioning near a site of administration;

5) ejecting the sterile fluid as a spray from the dispensing cap enclosure into or onto the site of administration without touching by depressing the actuator; and 6) replacing the dispensing cap enclosure when empty onto the main container body.

* * * * *